United States Patent [19]
Ahl et al.

[11] Patent Number: 6,051,389
[45] Date of Patent: Apr. 18, 2000

[54] ENZYME SENSOR

[75] Inventors: Thomas Ahl, Rungsted Kyst; Allan Milton Byrnard, Copenhagen S, both of Denmark

[73] Assignee: Radiometer Medical A/S, Denmark

[21] Appl. No.: 09/308,212

[22] PCT Filed: Nov. 7, 1997

[86] PCT No.: PCT/DK97/00508

§ 371 Date: Aug. 12, 1999

§ 102(e) Date: Aug. 12, 1999

[87] PCT Pub. No.: WO98/21356

PCT Pub. Date: May 22, 1998

[30] Foreign Application Priority Data

Nov. 14, 1996 [DK] Denmark .................................. 96/1285

[51] Int. Cl.⁷ .............................. C12Q 1/62; C12Q 1/60; C12Q 1/54; C12Q 1/42; C12Q 1/26
[52] U.S. Cl. .................................. 435/10; 435/11; 435/14; 435/17; 435/21; 435/25; 435/20; 435/283.1; 435/963; 435/973
[58] Field of Search .................................. 435/10, 25, 14, 435/11, 20, 21, 17, 283.1, 963, 973

[56] References Cited

U.S. PATENT DOCUMENTS

| | | | |
|---|---|---|---|
| 5,531,878 | 7/1996 | Vadgama et al. | 435/283.1 |
| 5,567,290 | 10/1996 | Vadgama et al. | 435/283.1 |

FOREIGN PATENT DOCUMENTS 244 567 A1 of 0000 Germany .

OTHER PUBLICATIONS

International Search Report dated Mar. 5, 1998 corresponding to PCT/EP97/06103.

Kuga et al., 1976, Mem. Fac, Sci. Kyushu Univer. Ser. C. 10, pp. 77–90; CA: 85:42969h.

Brown, et al., 1981, Makromol. Chem., 182, pp. 1605–1616.

Hu et al., 1993, Analytica Chimica Acta, 281, pp. 503–511.

Tsuchida et al., 1985, Cotechnology and Bioengineering, vol. 27, pp. 837–841.

Pfeiffer et al., 1992, Biosensors & Bioelectronics, 7, pp. 661–671.

Baker et al., 1995, Analytical Chemistry, vol. 67, No. 9, May 1, 1995, pp. 1536–1540.

Liu et al., 1995, Electrochemica Acta, vol. 40, No. 12, pp. 1845–1849.

Winckers et al., 1996, Clinical Chemistry, vol. 42, No. S6, poster No. 761.

Simonian, et al., 1997, Biosensors & Bioelectronics, vol. 12, No. 5, pp. 363–371.

Demura et al., 1989, Biosensors, vol. 4, pp. 361–372.

Johnson, 1979, Immobilized enzymes, preparaing and engineering, Noyes Data Corp., pp. 160–161.

*Primary Examiner*—Louise N. Leary
*Attorney, Agent, or Firm*—Bryan Cave LLP; Maurice B. Stiefel; Leo G. Lenna

[57] ABSTRACT

The present invention relates to an enzyme sensor for measuring the concentration or activity of an analyte in a test fluid. The sensor has at least one enzyme layer comprising an immobilized enzyme for which the analyte is a substrate. The immobilized enzyme is obtained by formation of one or more covalent link(s), optionally by using a cross-linking agent, between the enzyme and at least one type of macromolecule in the presence of a competitive inhibitor for said enzyme. The present invention also relates to a membrane for an enzyme sensor. Furthermore, the invention relates to a method for stabilizing the enzymatic activity of an enzyme sensor.

32 Claims, 3 Drawing Sheets

ENZYME SENSOR

FIELD OF THE INVENTION

The present invention relates to an enzyme sensor for measuring the concentration or activity of an analyte in a test fluid and to a membrane for an enzyme sensor, which have been improved with respect to initial specific enzymatic activity. The present invention also relates to a method for improving the enzymatic stability (the lifetime) of enzyme sensors in general.

BACKGROUND OF THE INVENTION

Enzyme sensors are sensors where a chemical species to be measured (an analyte) undergoes an enzyme catalysed reaction in the sensor before detection. The reaction between the analyte and the enzyme (for which the analyte should be a substrate) yields a secondary species which concentration (under ideal conditions) is proportional with or identical to the concentration of the analyte. The concentration of the secondary species is then detected by a transducer, e.g., by means of an electrode.

The enzyme of an enzyme sensor is typically included in a membrane suited for contacting the test fluid. The enzyme may be included as part of a membrane of a sensor or may be located behind such a membrane. Another alternative is to incorporate the enzyme into the sensor proper, e.g. as part of a carbon paste layer of an electrode. Hence, the analyte is contacted with the enzyme after diffusion into the outer part of the sensor (e.g. the membrane or the carbon paste layer), the enzyme/analyte reaction takes place, and the secondary species then diffuses to the detector part of the sensor, e.g. an electrode.

In a traditional enzyme sensor comprising a membrane, the membrane must, on the one hand, have a suitable porosity so that the analyte diffuses from the test fluid to the enzyme in a controlled manner, and, on the other hand, be impermeable or substantially impermeable to the enzyme in question in order to avoid leaching of the enzyme into the test fluid.

One way to overcome this problem is to immobilize the enzyme in question to a macromolecule so that the physical size and the general low solubility of the enzyme/macromolecule prohibit leaching through the porous membrane. A possible alternative, which may be more suited for in-situ polymerized membranes, could be to entrap the enzyme in polymers.

An interesting example of an analyte which is present in, e.g., body fluids is lactate. Lactate sensors wherein lactate oxidase is immobilized to bovine serum albumin are known (Hu et al., 1993, Analytica Chimica Acta, 281, pp 503–511; Tsuchida et al., 1985, Biotechnology and Bioengineering, 27, pp 837–841; Pfeiffer et al., 1992, Biosensors & Bioelectronics, 7, pp 661–671; Baker et al., 1995, Anal. Chem., 67, pp 1536–1540; and Liu et al., 1995, Electrochemica Acta, 40, pp 1845–1849). The reported lifetime of lactate sensors is typically around 14 days (see for example Winckers et al., 1996, Clinical Chemistry, 42, No. S6, p S278, poster No. 761).

Typically, when an enzyme, e.g. lactate oxidase, is immobilized, the initial specific enzymatic activity of the immobilized enzyme is reduced compared to a corresponding amount of non-immobilized enzyme. This may be due to the fact that the enzyme, or at least a part (a domain) thereof, does not retain its active conformation during or after the immobilization reaction, or that the immobilization reaction involves functional groups of the enzyme which are situated in or very close to the active site of the enzyme. Thus, a considerable amount of enzyme may be inactivated in the immobilization reaction. The presence of large amounts of inactivated, partially inactivated or denatured enzyme in a sensor is highly undesirable as this may lead to longer response times.

It has been reported that immobilization of trypsin to a solid phase material in the presence of a competitive inhibitor results in almost full retention of the initial specific enzymatic activity (Kuga et al., 1976, Mem. Fac. Sci. Kyushu Univ. Ser. C, 10, pp 77–90; CA: 85:42969h). It has also been described to use a polymeric competitive inhibitor when immobilizing trypsin to water-insoluble carriers (Brown et al., 1981, Makromol. Chem., 182, pp 1605–1616). Neither of these publications addresses the use of immobilized trypsin in an enzyme sensor, and, to applicant's best knowledge, no other publications address the use of immobilized trypsin in an enzyme sensor. Thus, the special conditions and requirements applying for immobilized enzymes for enzyme sensors have not been addressed or rendered obvious.

The aim of the present invention is to provide enzyme sensors which have an improved initial specific enzymatic activity. Another aim of the present invention is to provide a method for stabilizing the enzymatic activity of enzyme sensors so that the lifetime of enzyme sensors can be prolonged.

SUMMARY OF THE INVENTION

The applicant has now found that enzymes immobilised in the presence of a competitive inhibitor are especially suited for enzyme sensors where a high (initial) ratio between active and inactive enzyme is desirable/required.

Thus, the present invention provides an enzyme sensor for measuring the concentration or activity of an analyte of a test fluid, the sensor having at least one enzyme layer comprising an immobilized enzyme for which the analyte is a substrate, the immobilized enzyme being obtained by formation of one or more covalent link(s), optionally by using a cross-linking agent, between the enzyme and at least one type of macromolecule in the presence of a competitive inhibitor for said enzyme.

It is considered non-obvious to utilise immobilized enzymes immobilised in the presence of a competitive inhibitor in an enzyme sensor. The skilled person would tend to conclude that the competitive inhibitor might have a negative influence on the subsequent measuring properties of the sensor.

The enzyme layer may be applied to the sensor in various ways. Thus, the enzyme layer may be included as part of a membrane of a sensor or may be located behind such a membrane. Alternatively, the enzyme layer may be an integral part of the sensor, e.g. included in a carbon paste layer of an electrode. In a preferred embodiment the enzyme layer is included in a membrane to be mounted to the sensor.

The present invention also provides a membrane for an enzyme sensor for measuring the concentration or activity of an analyte in a test fluid, said membrane having an enzyme layer comprising an immobilized enzyme for which the analyte is a substrate, the immobilized enzyme being obtained by formation of one or more covalent link(s), optionally by using a cross-linking agent, between the enzyme and at least one type of macromolecule in the presence of a competitive inhibitor for said enzyme.

It is believed that enzyme sensors and membranes prepared as defined above result in enzyme sensors and membranes having hitherto unsurpassed high initial specific enzymatic activities compared to conventionally prepared sensors and membranes.

The present invention further provides an enzyme sensor or measuring the concentration or activity of an analyte of a test fluid, the sensor having at least one enzyme layer comprising an immobilized enzyme for which the analyte is a substrate, the initial specific enzymatic activity of the immobilized enzyme being at least 50% of the initial specific enzymatic activity of a corresponding amount of non-immobilized enzyme, determined in the same test.

The enzyme may be applied to the sensor as described above.

Further, the present invention provides a membrane for an enzyme sensor for measuring the concentration or activity of an analyte of a test fluid, said membrane having at least one enzyme layer comprising an immobilized enzyme for which the analyte is a substrate, the initial specific enzymatic activity of the immobilized enzyme being at least 50% of the initial specific enzymatic activity of a corresponding amount of non-immobilized enzyme.

In addition, it has been found, in contrast to what should be believed, that the presence of a competitive inhibitor in the enzyme sensor is advantageous not only during the immobilization reaction, but also afterwards. The applicant has found that it may be especially advantageous to expose the immobilized enzyme included in a sensor to a competitive inhibitor in order to increase the stability of the enzymatic activity and thereby increase the lifetime of a sensor.

Thus, the present invention also provides a method for improving the stability of the enzymatic activity of an immobilized enzyme included in an enzyme sensor, comprising intermittently or continuously exposing the immobilized enzyme to a solution comprising a competitive inhibitor for said enzyme.

The improved stability is obtained both for an enzyme sensor with an immobilized enzyme obtained by formation of covalent link(s) between the enzyme and a macromolecule in the presence of a competitive inhibitor for the enzyme and for an enzyme sensor with an immobilized enzyme obtained as above, but in the absence of a competitive inhibitor, as well as for any other enzyme sensor with an immobilized enzyme.

As mentioned above, the present invention provides novel and highly valuable enzyme sensors and membranes for enzyme sensors. Enzyme sensors have become increasingly important for analytical purposes in that it is desirable, as a matter of routine, to analyse a large number of test fluids with respect to the concentration (or activity) by using fully automatic apparatuses. An example of a fully automatic analysis apparatus for handling biological samples, and for which the novel enzyme sensors are especially suited, is the ABL™ System 625 Blood Gas System (Radiometer Medical A/S, Copenhagen, Denmark). Such a system is, from the user's side, expected to allow for long operating times ("up" time) and very short and rare service times ("down" time). Thus, enzyme sensors used in such apparatuses should have a long lifetime. The present invention provides long-life enzyme layers for enzyme sensors.

The analyte to be measured by the enzyme sensor may be any substance which is a substrate for an enzyme which can be included in the membrane of a sensor. Especially interesting analytes in the present context are glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine. An especially relevant analyte in the present context is lactate. Other analytes that might be interesting to measure are glycated amino acids, coagulation factors and sepsis markers.

The selection of a relevant enzyme for a sensor is naturally directed by the analyte. It should also be considered that one of the reaction product(s) of the enzyme/analyte reaction (the secondary species) must be detectable either directly or after subsequent conversion into a detectable substance. A preferred secondary species is hydrogen peroxide which may be detected by conventional electrodes.

This being said, preferred enzymes in the present context are those for which an analyte selected from the group consisting of glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine is a substrate.

Particularly interesting enzymes are selected from the group consisting of α-hydroxy oxidase (E.C.1.1.3.15), lactate oxidase (E.C.1.1.3.2), glucose oxidase (E.C.1.1.3.4), urease (E.C.3.5.1.5), creatine amidohydrolase (E.C.3.5.2.10), creatine amidinohydrolase (E.C.3.5.3.3), sarcosine oxidase (E.C.1.5.3.1), glutamate dehydrogenase (E.C.1.4.1.3), pyruvate kinase (E.C.2.7.1.40), long chain alcohol oxidase (E.C.1.1.3.20), and lactate dehydrogenase (E.C.1.1.1.27), among which lactate oxidase is especially preferred.

The analyte may in principle be present in any type of test fluid, thus, in the present context the term "test fluid" is intended to mean any liquid comprising an analyte which concentration or activity it is desirable to measure.

Limitations with respect to the nature of the test fluid will often be set by the materials selected for the enzyme sensor and, in particular, the membrane. Preferably, the test fluid is an aqueous test fluid, e.g. a test fluid of natural origin.

Especially interesting test fluids in the present context are biological samples from animals or humans, especially from humans. Such biological samples may either be used directly or they may be diluted or treated in various ways in order to remove species which would otherwise interfere with the enzyme, the detector, or the analyte. Examples of biological samples are whole blood, e.g. diluted or undiluted whole blood, blood plasma, blood serum, cerebrospinal fluid, synovial fluid, urine, saliva, and milk. Other interesting test fluids are e.g. dialysis fluids.

The present invention takes advantage of competitive inhibitors in immobilization reactions and subsequently as stabilizing agent. Without being bound to any specific theory, it is believed that the presence of a competitive inhibitor, when covalent links between an enzyme and (a) macromolecule(s) are formed, eliminates or reduces the risk of chemical functionalities in the active site of the enzyme (the site to which a substrate for the enzyme is bound when the enzymatic action is expressed) taking part in the covalent link formation reaction. Thus, it is believed that in the cases where no competitive inhibitor is present, chemical functionalities in the active site, e.g. amino and guanidino groups of lysines and arginines, respectively, may be involved in the covalent bond formation reaction whereby the enzyme activity is reduced or eliminated.

A competitive inhibitor for a specific enzyme is characterised in that it binds in, or in the close proximity of, the active site of the enzyme so that a substrate for the enzyme is obstructed from immediately occupying the active site. However, depending on the affinity (for the enzyme in question) and concentration of the competitive inhibitor in relation to the affinity (for the enzyme in question) and concentration of the substrate, there will be a competition (cf. "competitive") between the inhibitor and the substrate for occupation of the active site.

Suitable competitive inhibitors may be any of the competitive inhibitors for the enzyme in question known in the art. Also, "partial" competitive inhibitors are to be construed as competitive inhibitors in the present context. However, it is believed that competitive inhibitors especially relevant in the present context are those which, on the one hand, binds efficiently to the enzyme in question during the immobilization reaction and, on the other hand, can be replaced by the substrate (the analyte) for the enzyme in question when the immobilized enzyme is included in the enzyme sensor. It is envisaged that especially suitable competitive inhibitors are those which have an affinity ($1/K_i$) for the enzyme in question which is about 0.0001 to 10 times, such as 0.001 to 5 times, the affinity of the substrate for the same enzyme.

For one of the most interesting enzymes in the present context, i.e. lactate oxidase, preferred competitive inhibitors are selected from the group consisting of oxalacetate, oxalate, α-hydroxy-sulphonate, bisulphite, and phenylacetate. Oxalate has proved to be especially preferred.

Analogous to the presence of competitive inhibitors it should also be understood that any coenzymes necessary for the enzyme to exhibit enzymatic activity is present during the immobilisation reaction so that (i) the immobilisation reaction is performed when the enzyme is present in an active conformation and (ii) the site to which the coenzyme is attached is not blocked by covalent links to the macromolecule(s).

In the present context the term "macromolecule" is to be understood as a high molecular weight molecule, which may be the enzyme proper. The macromolecule should have a chemical functionality which allows for the formation of covalent bonds between the macromolecule and the enzyme in question. It should be understood that the macromolecule may be of natural origin as well as synthetic origin (e.g. a synthetic organic polymer).

Examples of macromolecules of natural origin are proteins, e.g. albumins and albumin derivatives, such as serum albumin (e.g. bovine serum albumin and bovine serum albumin-cysteinyl), conalbumin (ovotransferrin), ovalbumin (egg white albumin), lactalbumin, grain albumin, and soybean albumin.

Examples of macromolecules of synthetic origin are polymeric compounds such as polyolefins and derivatives thereof, e.g. polyethylene, polypropylene, polystyrene, and poly(meth)acrylate, polyester, polyethers, polyalkylene glycols, e.g. polyethylene glycol, polypropylene glycol, and polybutylene glycol, polyamides, and synthetic polypeptides, dextrans, and proteins.

Of the above-mentioned relevant examples, macromolecules selected from the group consisting of albumins and albumin derivatives, such as bovine serum albumin, boyine serum albumin-cysteinyl, conalbumin (ovotrans-ferrin), and ovalbumin (egg white albumin), are especially preferred.

The weight average molecular weight of macromolecules particularly relevant in connection with immobilizing of enzymes is from 10,000, such as from 10,000 to 1,000,000, preferably 10,000 to 200,000, in particular 20,000 to 100,000.

The immobilisation reaction (cross-linking reaction) may be performed either by direct reaction between the enzyme and the macromolecule or by using a cross-linking agent. Usually a cross-linking agent is required. Cross-linking agents are known to the person skilled in the art, however, especially preferred cross-linking agents for the enzymes described herein are selected from the group consisting of glutaraldehyde, divinyl sulphone, cyanuric chloride, diisocyanates, polyisocyanates, diisothiocyanates, and polyisothiocyanates, among which glutaraldehyde is preferred.

The degree of cross-linking should be so that, on the one hand, leaching of the immobilized enzyme is avoided and, on the other hand, the mobility of the various domains of the enzyme is maintained (otherwise the enzymatic activity will be hampered). It is believed that a weight average molecular weight of the enzyme/macromolecule conjugate (the immobilized enzyme) should be at least 100,000, preferably in the range of 100,000 to 5,000,000, in particular 200,000 to 4,000,000, in order for the immobilized enzyme to become unable or substantially unable to diffuse through the outer layer of an enzyme sensor, e.g. a diffusion limiting layer (see further below), and at the same time be sufficiently soluble or dispersible in an aqueous medium, e.g. a buffer, so that handling is possible prior to inclusion in a membrane.

The immobilized enzymes are preferably prepared as follows: (a) a solution comprising the enzyme, at least one type of macromolecules, and a competitive inhibitor for said enzyme is prepared; and (b) a cross-linking agent is added to the solution. Furthermore, (c) a quenching reagent may be added after the desired reaction time in order to inactivate any remaining cross-linking agent and effectively terminate the reaction. Quenching reagents are reagents which react with the cross-linking agent or any intermediate derived from the cross-linking agent.

It is believed that thorough mixing of the solution comprising the enzyme, the macromolecule, and the competitive inhibitor should be performed in order to establish an equilibrium between dissolved competitive inhibitor and enzyme-bound competitive inhibitor.

The cross-linking reaction should preferably take place at a temperature in the range of 0–40° C., more preferably in the range of 10–30° C., so that the enzyme is not denatured during the cross-linking reaction. Preferably the cross-linking reaction is performed at ambient temperature.

With respect to the reaction medium, it is believed that an aqueous medium is preferred over an organic media. The aqueous medium should preferably be a buffer adjusted to the a pH value in the range of 5.0–9.0, in particular in the range of 6.0–8.0. Phosphate buffers are especially preferred.

In an embodiment of the present invention, immobilized lactate oxidase for the sensor is prepared from 4–7 parts by weight, such as 5–6 parts by weight, of lactate oxidase, 8–12 parts by weight, such as 9–11 parts by weight, of bovine serum albumin-cysteinyl, and 1.5–3.5 parts by weight, such as 2–3 parts by weight, of cross-linking agent using 12–15 parts by weight, such as 13–14 parts by weight, of sodium oxalate (see Example 1).

It should be understood that it may be advantageous to add a competitive inhibitor for the enzyme in the case where the immobilized enzyme is to be stored before inclusion in a sensor or a membrane for a sensor.

The enzyme of an enzyme sensor is typically included in a membrane suited for contacting the test fluid.

The membranes according to the invention are preferably membranes comprising an enzyme layer included as part of a membrane or located behind such a membrane. The membrane may serve several purposes including providing protection from potentially harmful substances in the test fluid, ascertaining retention of the enzyme in the membrane and providing optimal diffusion limiting conditions for the analyte to be measured in order to obtain sufficient linearity for the sensor.

Thus, it is preferred that the membranes comprise a diffusion limiting layer which is adapted to separate the enzyme layer and the test fluid. The diffusion limiting layer is a porous membrane layer which limits the diffusion of the analyte into the enzyme layer so that the capacity of the immobilized enzyme for conversion of the analyte is not exceeded, and so that sufficient $O_2$ for the enzymatic conversion of the analyte is present in the enzyme layer. The principle of diffusion limiting layers is described in Danish Patent No. 170103.

The diffusion limiting layer may consist of a membrane of a type normally used for sensors. These comprise solution/diffusion type membranes (e.g. hydrogels), track etch membranes (having straight pores), composite membranes and tortuous path membranes.

The material for the diffusion limiting layer may include any membrane material for sensors known in the art. Examples are polyolefins and derivatives thereof, e.g. polyethylene, polypropylene, polystyrene, and poly(meth)acrylate, polyester, polyethers, polyalkylene glycols, e.g. polyethylene glycol, polypropylene glycol, and polybutylene glycol, polyamides, silicones and regenerated cellulose. Polyesters such as polyethylene terephthalate may be especially suitable. Other polymers such as e.g. polycarbonates and polyurethanes may be useful as well.

In a preferred embodiment the diffusion limiting layer has through-going pores which are permeable to the analyte and impermeable or substantially impermeable to the immobilized enzyme, and at least a part of the pores should, of course, extend from the surface of the diffusion limiting layer adapted to face the test fluid to the surface of the diffusion limiting layer adapted to face the enzyme layer.

It should be understood that the through-going pores of the diffusion limiting layer have walls, and that the surface of these walls together with the surface adapted to face the test fluid define an accessible surface of the diffusion limiting layer, i.e. the surface accessible to the test fluid. This accessible surface of the diffusion limiting layer should preferably be hydrophilic so that, e.g., blood proteins do not become attached to the surface. Thus, the accessible surface of the diffusion limiting layer may, if it is not in itself sufficiently hydrophilic, have derivatisable chemical groups of which at least a part are derivatised with a hydrophilic component whereby the accessible surface is rendered more hydrophilic than a corresponding non-derivatized surface.

The derivatisable chemical groups may be present in the natural form of the membrane layer material, or they may arise after treatment of the membrane layer material with a chemical reagent, or after irradiation of the membrane.

The hydrophilic component should be selected so that the surface treated membrane layer is not degraded under the normal cleaning and rinse conditions applicable for enzyme sensors. Thus, it is envisaged that polyalkylene glycols such as polyethylene glycol (PEG), heparin, hyaluronic acid, phospholipids, agarose, chitosan, cyclodextrin, alginate, collagen, lignin, pectin as well as polysaccharides and cellulose-based polymers such as dextrin, hydroxyalkylceiluloses, cellulose acetates, albumin, gelatine, agar, carageenans, and starch are suited as hydrophilic components. Also, hydrophilic synthetic organic polymers, e.g. polyvinylalcohol/polyvinylacetates, polyvinylpyrrolidone, hydroxyalkyl(meth)acrylates such as hydroxymethyl(meth)acrylate and hydroxyethyl(meth) acrylate, (meth)acrylic acid, allylalcohol, and acrylpolymers (hydrogels) may be used.

Among these possible hydrophilic components, polyethylene glycol and heparin are especially interesting. Furthermore, polyethylene glycols having an average molecular weight of from about 100 to about 2000, such as from about 200 to about 1000, are believed to be especially relevant as hydrophilic components.

It should be understood that for practical reasons, often the entire surface of the membrane layer and the pores are modified, i.e. also the surface of the membrane layer adapted to face the enzyme layer.

The membrane according to the invention may further comprise an interference eliminating layer which is permeable to the product from the enzyme/analyte reaction and impermeable or substantially impermeable to the analyte and the immobilized enzyme. The interference eliminating layer should preferably also be impermeable to other chemical components which may be present in the test fluid. A very suitable material, which is impermeable to, e.g., HEPES, ascorbic acid, and paracetamol and permeable to, e.g., $H_2O_2$, is cellulose acetate.

Thus, in an embodiment of the present invention, the membrane comprises:

(a) a diffusion limiting layer comprising polyethylene terephthalate, the accessible surface of the diffusion limiting layer having carboxyl groups, at least a part of these carboxyl groups being derivatised by covalently linking thereto polyethylene glycol having an average molecular weight in the range of 100–1000;

(b) an enzyme layer comprising immobilized lactate oxidase, and (c) an interference limiting layer comprising cellulose acetate.

The individual membrane layers are cut in congruent pieces and are assembled, e.g., in a membrane ring. The membrane preferably has a thickness in the range of 10–50 $\mu$m, in particular in the range of 10–30 $\mu$m. The diffusion limiting porous membrane layer is preferably 5–20 $\mu$m, the enzyme layer is preferably 1–3 $\mu$m, and the interference limiting layer is preferably 5–10 $\mu$m.

The sensor according to the present invention may be based on one or several applicable detector principles, such as electrochemical or optical principles. Thus, the detector part face of the sensor may, e.g., be a part of an electrode or an optical detector. Preferably, the detector part of the sensor is a part of an electrode.

An electrode may comprise an anode of e.g. carbon paste or platinum, gold, iridium, rhodium, palladium and alloys or pastes thereof, and a reference electrode of e.g. silver/silver chloride, silver/silver oxide, or mercury/mercury(I) chloride. The electrode may further comprise any necessary electrolyte solution. Preferably, the electrode comprises a platinum anode and silver/silver chloride reference electrode.

As it has been described above, the present invention provides enzyme sensors and membranes for enzyme sensors where the initial specific enzymatic activity has been improved. Thus, in an embodiment of the present invention, the initial specific enzymatic activity of the immobilized enzyme included in a membrane for an enzyme sensor is at least 50% of the initial specific enzymatic activity of a corresponding amount of non-immobilized enzyme. Preferably and also realistically, the initial specific enzymatic activity is at least 60%, such as at least 70%, in particular at least 80% or even at least 90%, compared to the initial specific enzymatic activity of a corresponding amount of non-immobilized enzyme.

In Example 4, the initial specific enzymatic activity for immobilized lactate oxidase is 78% (Table 1). Thus, immobilized lactate oxidase prepared as described in Example 4 will, when incorporated in a membrane for an enzyme sensor, constitute a preferred embodiment of the present invention.

In a further embodiment of the present invention, the initial specific enzymatic activity of the immobilized enzyme is at least 1.5 times the initial specific enzymatic activity of a corresponding amount of enzyme immobilized to the same kind of macromolecule by using, if applicable, the same kind of cross-linking agent in the absence of a competitive inhibitor for said enzyme. In Example 4, it has been shown that immobilised lactate oxidase fulfils this criteria, cf. Table 1.

As it should be clear from the above, the present invention provides enzyme sensors and membranes for enzyme sensors which may be designed so that they have an hitherto unsurpassed lifetime. Thus, when using a specific amount of (non-immobilized) enzyme in the immobilization reaction defined herein, the initial specific enzymatic activity is higher than when using conventional conditions, and, consequently, the period before the enzymatic activity reaches the level where the sensor becomes unusable is prolonged.

Apart from the novel long-life enzyme sensors, the applicant has found that storage of enzymes in a medium comprising a competitive inhibitor for the enzyme improves the stability of the enzymatic activity (see Example 5). Thus, as mentioned above, the present invention provides a method for improving the stability of the enzymatic activity of an immobilized enzyme included in an enzyme sensor for measuring the concentration of an analyte in a test fluid, the analyte being a substrate for the enzyme, the method comprising intermittently or continuously exposing the immobilized enzyme to a solution comprising a competitive inhibitor for said enzyme.

With respect to the definition of the sensor, enzyme, and competitive inhibitor, etc., the definitions and preferred embodiments mentioned above also apply here. Thus, the immobilized enzyme may be included as an integral part of the sensor, or included in a membrane of the enzyme sensor.

It should be understood that the method may be equally applicable in the case where a replacement membrane for an enzyme sensor has to be stored before it is mounted to the sensor. Thus, the present invention also provides a method for improving the stability of the enzymatic activity of an immobilized enzyme included in a membrane for an enzyme sensor.

In a very interesting embodiment where the method is performed for an enzyme sensor either used separately or included in a fully automatic apparatus, the enzyme layer comprising the immobilized enzyme is exposed to a solution comprising a competitive inhibitor for said enzyme between each or substantially each measurement, or between each or substantially each series of measurements, of the analyte. Thus, in order to optimize the rinsing process for a sensor and avoid that the exposure of the enzyme layer to the competitive inhibitor becomes a separate operation step, the competitive inhibitor may be included in the rinse fluid for said sensor.

The concentration of the competitive inhibitor in the rinse fluid should preferably be so that, when the enzyme in question is permanently stored in the rinse fluid comprising the competitive inhibitor at that specific concentration, the increase in $t_{1/2}$ for the enzymatic activity would be at least 50%, such as at least 100%, in particular at least 200%.

Relevant competitive inhibitors which, on the one hand, have the ability to efficiently stabilize an enzyme composition, especially an immobilized enzyme composition, and, on the other hand, allow for the enzymatic reaction to take place in the (simultaneous) presence of a substrate for the enzyme, are those which have a binding affinity for the active site of the enzyme which is equal to, or slightly lower than, the binding affinity of the relevant substrate.

In an especially interesting embodiment, the method is performed for lactate oxidase included in an enzyme sensor for measuring lactate in a biological sample.

This highly valuable principle for stabilizing the enzyme activity may be used for enzyme sensors in general, thus, the present invention also relates to the use as a stabilizing agent for an immobilized enzyme included in an enzyme sensor of a solution comprising a competitive inhibitor for said enzyme. Such a solution may be a rinse or cleaning fluid for the sensor. It should, however, be noted that a solution comprising a competitive inhibitor may also be used for the stabilisation of non-immobilized enzymes or enzymes which have been immobilized in other ways than described herein.

The enzyme sensors and the membranes described herein are especially suited for use in fully automatic apparatuses for measuring the concentration or activity of one or more analytes in a test fluid. In such commercially available fully automatic apparatuses it is possible, even with only minor reconstruction efforts or replacement of the rinse fluid(s) for the enzyme sensor(s), to utilize the method according to the invention.

Thus, the present invention also provides an apparatus for measuring the concentration or activity of one or more analytes of a test fluid, the apparatus comprising an enzyme sensor having a layer of an immobilized enzyme for which at least one of the analytes is a substrate, wherein the apparatus further comprises one or more containers with solution(s) needed for the operation of the apparatus, at least one solution comprising a competitive inhibitor for the enzyme, and means for intermittently exposing the sensor to the solution comprising the competitive inhibitor.

DETAILED DESCRIPTION OF THE INVENTION

Figure 1:
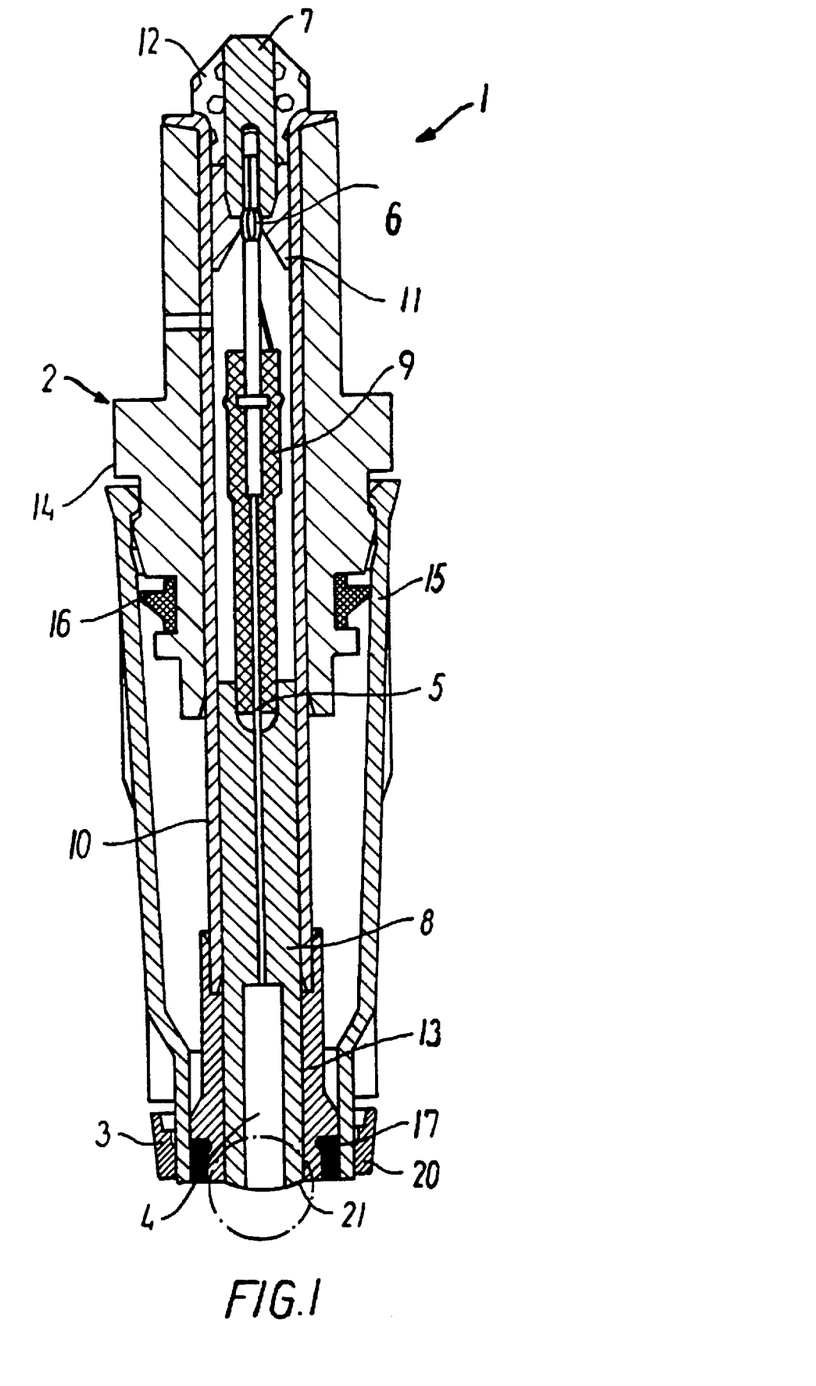
FIG. 1 illustrates an enzyme sensor 1 comprising an electrode and a membrane.

FIG. 1 shows an enzyme sensor 1 for measuring lactate. Enzyme catalysed reaction between lactate and oxygen yields hydrogen peroxide ($H_2O_2$) and pyruvate. Hydrogen peroxide is then detected by an amperometric electrode. The sensor 1 is suited for mounting in an apparatus for measuring the concentration of analytes in a biological sample, e.g. an ABL™ 625 Blood Gas System (Radiometer Medical A/S, Copenhagen, Denmark).

Basically, the sensor 1 comprises an electrode 2 onto which a membrane ring 3 is attached. The electrode 2 comprises a platinum anode 4 connected with a platinum wire 5, which, through a micro plug 6, is connected with an silver anode contact body 7. The platinum anode 4 and the lower part of the platinum wire 5 is sealed into a glass body 8. Between the glass body 8 and the micro plug 6, the platinum wire 5 is protected with a heat shrink tubing. A tubular silver reference electrode 10 encircles the upper part of the glass body 8 and extends in the length of the electrode 2 to the anode contact body 7, which is fastened inside the reference electrode by means of a fixing body 11 and epoxy 12. The lower part of the glass body 8 is surrounded by an electrode base 13 whereto the membrane ring 3 is attached.

The upper part of the reference electrode 10 is surrounded by a plug part 14 for mounting the electrode 2 in the corresponding plug of an analysis apparatus (not shown) and for fixing a mantle 15. Gaskets 16 and 17 are placed between the electrode 2 and the mantle 15 in order to ensure that any electrolyte located at the measuring surface of the electrode 2 does not evaporate. The membrane ring 3, which is mounted at one end of the mantle 15, comprises a ring 20. A membrane 21 is stretched over the lower opening of the ring 20. This membrane 21 is shown in detail in FIG. 2.

Figure 2:
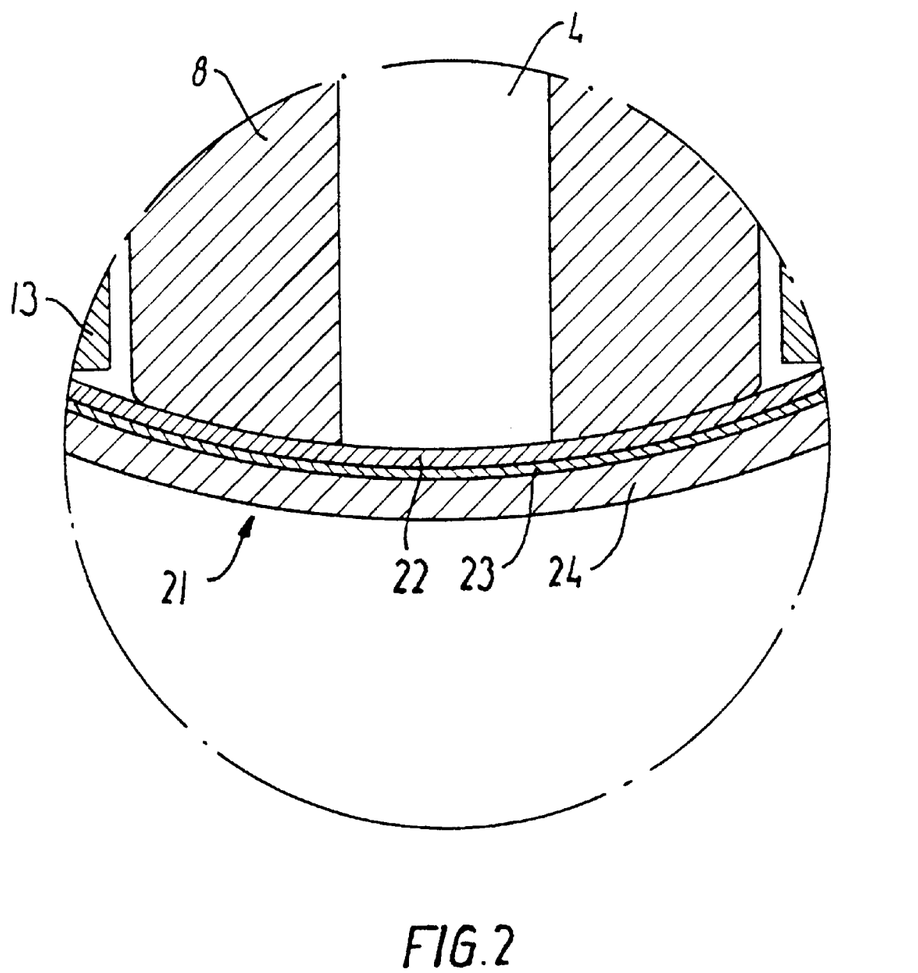
FIG. 2 illustrates in detail the membrane part of the membrane of FIG. 1.

FIG. 2 shows a membrane 21 comprising three layers: an interference limiting membrane layer 22 facing the platinum anode 4 of the electrode 2, an enzyme layer 23, and a diffusion limiting porous membrane layer 24 facing the test fluid. The interference limiting membrane layer 22 may be a 6±2 $\mu$m porous membrane of cellulose acetate (CA). The enzyme layer is typically an approx. 1–2 $\mu$m layer of cross-linked lactate oxidase (7 units/membrane). The diffusion limiting porous membrane layer 24 may be an approx. 10 $\mu$m layer of polyethylenetherephthalate (PETP) (pore diameter approx. 0.1 $\mu$m; pore density: $8 \cdot 10^5$ pores/cm$^2$).

Figure 3:
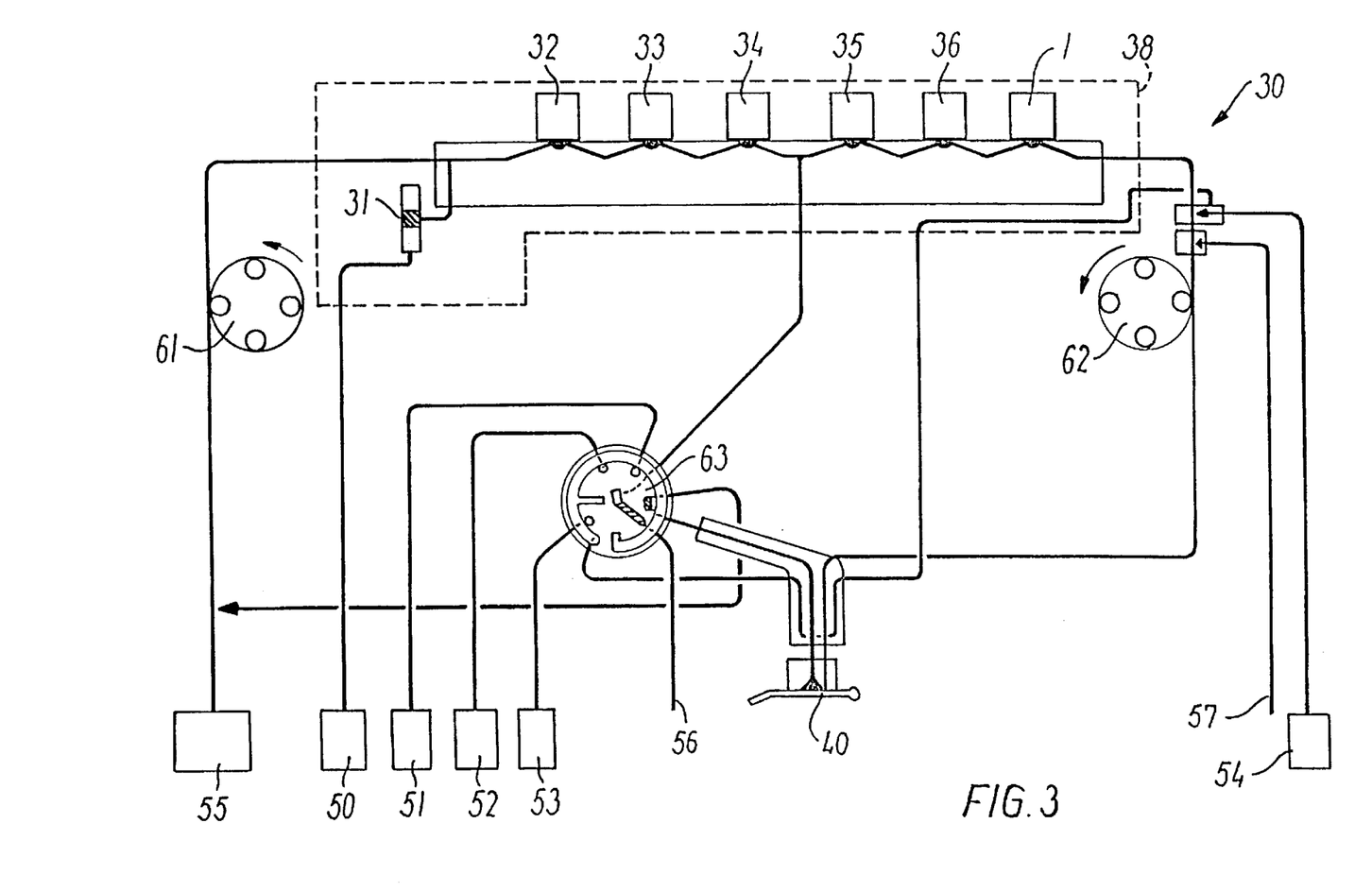
FIG. 3 illustrates in schematic form an embodiment of an apparatus according to the invention.

FIG. 3 shows in schematic form an embodiment of an apparatus 30 according to the invention. The apparatus 30 comprises several sensors 1, 31–36 for measuring the concentration or activity of different analytes in a test fluid. The sensors include a reference electrode 31, sensors for measuring e.g. pH, p$O_2$, p$O_2$, etc. 32–36 and an enzyme sensor 1 for measuring lactate similar to the sensor described above in connection with FIGS. 1 and 2. The sensors 1, 31–36 are located in a measuring section shown by the dotted line 38.

The apparatus 30 has an inlet 40 for introduction of a test fluid into the apparatus 30 and several containers 50–54 with solutions needed for the operation of the apparatus 30. Thus, the container 50 comprises a salt-bridge solution for the reference electrode 31, the containers 51 and 53 comprise different calibration solutions for the sensors 1, 32–36, the container 52 comprises a cleaning solution for the sensors 1, 32–36 and finally the container 54 comprises a rinse solution for the sensors 32–36. The rinse solution of the container 54 comprises oxalate which as mentioned previously is a competitive inhibitor for the lactate oxidase enzyme in the lactate enzyme sensor 1.

The apparatus 30 further includes a waste container 55 and air inlets 56, 57. A fluid conduit system (shown in dark lines) connects the inlet 40, the containers 50–55 and the air inlets 56, 57 with the sensors 1, 31–36. Test fluid from the inlet, solutions from the different containers 50–54 and optionally air from the air inlets 56, 57 may be transferred in the fluid conduit system by means of pumps 61, 62 and a main valve 63 controlled by not shown software means of the apparatus 30.

When a test fluid has been introduced into the inlet, the pumps 61, 62 and the main valve 63 are activated to transfer the test fluid to the measuring section 28 and the test fluid is analyzed. Then the test fluid is transferred to the waste container 55. A rinse operation is now performed comprising activating the pumps 61, 62 and main valve 63 to transfer rinse fluid from the container 54 through the fluid conduit system to the sensors 1, 31–36 in the measuring section 28 and thence to the waste container 55. During this rinse operation the lactate enzyme sensor 1 is exposed to the oxalate contained in the rinse fluid. Thus, the lactate enzyme sensor 1 included in the apparatus 30 will be frequently exposed to the competitive inhibitor oxalate as this takes place in between each measurement performed on the apparatus 30.

TESTS SPECIFICATIONS

Enzyme Activity Test
   Colorimetric lactate oxidase assay
   Lactate oxidase (LOD) catalyses the reaction:

The formation of $H_2O_2$ is determined in a peroxidase (POD) assay system where a quinonimine dye is formed. The amount of formed quinonimine dye is determined spectrophotometically at 490 nm.
   Peroxidase catalyses the reaction:

Procedure:
Reagent A:
   2 mL 3,3-dimethylglutaric acid/NaOH (50 mM) buffer pH 6.5
   1 mL peroxidase (50 U/mL; 3.25 mg in 10 mL $H_2O$)
   1 mL 4-aminoantipyrine, 15 mM in $H_2O$
   1 mL DL-lactate 0.5 M, adjusted to pH 6.5 with NaOH
   3 mL $H_2O$
   2 mL 0.2% v/v 4-hydroxybenzenesulfonic acid in $H_2O$
   Enzyme Solution (enzyme composition to be tested):
   10 mL (immobilized) lactate oxidase (test solution approx. 0.04 U/mL in a 5 mM $KH_2PO_4$/NaOH buffer pH 7.0)
   Reference Enzyme Solution:
   10 mL lactate oxidase (Pediococcus) 0.04 U/mL in a 5 mM $KH_2PO_4$/NaOH buffer pH 7.0
   100 $\mu$L of Reagent A is added to a well of a microtiterplate (Immunoplate, Nunc, Roskilde, Denmark). The colour reaction is started by adding 100 $\mu$L of the Enzyme Solution. Immediately afterwards, the microtiterplate is placed in the plate-holder of a THERMOmax incubator (Molecular Devices, Menlo Park, Calif., USA) pre-set to: 37° C., kinetic mode, lag-time 5 min., reading time 15 min., and automix.
   In order to obtain a reference value for the initial specific enzymatic activity, 100 $\mu$L of the Reference Enzyme Solution is added to the well instead of the Enzyme Solution.
   Other enzymes may be tested in similar ways using the same reagents, in the case where the enzyme in question yields hydrogen peroxide, or other reagents sensible to the product of the enzyme/substrate reaction.
Enzyme Stability Test
   The enzymatic activity of lactate oxidase (and also other enzymes) is decreasing exponentially. Therefore, the half-life period ($t_{1/2}$) for the enzymatic activity will be independent of the initial concentration, and, thus, $t_{1/2}$ is an excellent expression for the stability of an enzyme under various conditions.
   The enzymatic activity is determined (as described in the Enzyme Activity Test above) for the enzyme composition in question at least four times over a relevant period, e.g. every day for at least four days (day 0 to day 3). $t_{1/2}$ is then calculated following standard mathematical methods.

EXAMPLES

Example 1

Preparation of Immobilized Lactate Oxidase

2720 Units of lactate oxidase and 40.0 mg bovine serum albumin-cysteinyl were dissolved in 400 µL 10 mM phosphate buffer (pH 7.0) and 1.60 mL 250 mM disodium oxalate. The mixture was mixed for 10 min. at 200 vibrations per min. 400 µL 2.5% (v/v aq.) glutaraldehyde was added, and the mixture was stirred for 10 min. The mixture was quenched with 100 µL 1 M glycine.

The immobilized lactate oxidase was ultra-filtered to a volume of 400 µL. Then, 400 µL of a 10 mM imidazole buffer (pH 7.0) containing 40% sucrose was added.

The final concentration of immobilized lactate oxidase was around 3400 U/mL.

Example 2

Preparation of Modified PETP Membrane Layer
Materials:
Mylar A polyethyleneterephthalate foil (Whatmann S. A., Louvain La-Neuve, Belgium) (thickness: 10 µm ±1 µm; pore diameter: approx. 0.1 µm; pore density: $8 \cdot 10^5$ pores/cm$^2$)

10 g PEG-200-(OH)$_2$ (polyethylene glycol having two hydroxy groups; average molecular weight 200 g/mole; minimum content of tetraethylene glycol: 20%; minimum content of tri-, tetra-, and pentaethylene glycol: 60%);

2 g CMC-MTS (1-cyclohexyl-3-(2-morpholinoethyl) carbodiimide metho-p-toluenensulfonate, 95%) as coupling reagent;

0.2 g Triton CF-54; and 4000 mL demineralised water (pH 6.0–6.5)

The PETP-material was cut in sheets and each sheet was fastened in a frame. The frame was suspended for 18 hours in a reaction mixture consisting of PEG-200-(OH)$_2$, CMC-MTS, Triton CF-54, and water. The sheets were then washed under stirring for 15 min. with 0.1% Triton X-100 in demineralized water, and subsequently washed twice with demineralized water for 2×10 min. Finally, the sheets were dried for at least 16 hours in a hood. All operations were performed at room temperature.

The PEG-200 chains on the surface of the membrane layer function as a hydrogel which makes the surface polar and non-reactive so that the ability for, e.g., blood proteins to attach to the surface is reduced or eliminated.

Example 3

Preparation of a Membrane

A cellulose acetate membrane of the type known in the art, e.g. as described in U.S. Pat. No. 3,979,274 was prepared.

2.0 µL of the solution comprising the immobilized lactate oxidase (Example 1) was dispensed to the cellulose acetate membrane layer. The surface modified PETP membrane layer was placed over the cellulose acetate/enzyme layer, and the membrane "sandwich" was allowed to dry.

The membrane could then be incorporated in a membrane ring for an enzyme sensor.

Example 4

Effect of Using Oxalate in Cross-Linking Reactions

Three enzyme solutions, A, B, and C were prepared as follows:

Basis Solution 20 mg (680 units) lactate oxidase and 10 mg bovine serum albumin-cysteinyl were dissolved in 100 µL 10 mM phosphate buffer (pH 7.0) under stirring for 5 min. 25 µL of this solution was used for each of the solutions A–C.

Enzyme Solution A

100 µL 250 mM disodium oxalate was added to the basis solution followed by stirring for 5 min. 25 µL 2.5% (v/v aq.) glutaraldehyde was added and stirring was continued for 10 min. and then 6.25 µL 1 M glycine was added.

Enzyme Solution B (without competitive inhibitor)

100 µL distilled water was added to the basis solution followed by stirring for 5 min. 25 µL 2.5% (v/v aq.) glutaraldehyde was added and stirring was continued for 10 min. and then 6.25 µL 1 M glycine was added.

Enzyme Solution C (without cross-linking agent)

100 µL 250 mM disodium oxalate was added to the basis solution followed by stirring for 5 min. 25 µL distilled water was added and stirring was continued for 10 min. and then 6.25 µL 1 M glycine was added.

Each of the solutions were diluted to 0.04 U/mL with a 10 mM imidazole buffer (pH 7.0).

The stability of the compositions were determined in the Stability Test described herein.

The initial specific enzymatic activity of Enzyme solutions A and B were compared to the initial specific enzymatic activity of the reference (Enzyme solution C).

TABLE 1

| % initial specific enzymatic activity | |
|---|---|
| Solution A | Solution B |
| 78% | 37% |

The results in Table 1 show that the initial specific enzymatic activity after cross-linking of lactate oxidase in the presence of oxalate is 78% compared with the initial specific enzymatic activity of the reference non-immobilized enzyme. Cross-linking in the absence of oxalate results in an initial specific enzymatic activity of only 37%.

Example 5

Oxalate as Stabilising Agent for Lactate Oxidase

Oxalate is a competitive inhibitor for lactate oxidase. Oxalate presumably binds to the active site of the enzyme, and it is therefore believed that oxalate will stabilize the enzymatic activity of lactate oxidase in that the enzyme is "locked" in the active conformation when oxalate is present.

A solution of 0.04 U/mL lactate oxidase in S4932 rinse solution (Radiometer Medical A/S, Copenhagen, Denmark) was prepared. Disodium oxalate corresponding to a total concentration of 1, 2, 4, 8, and 16 mM of oxalate was added. The enzymatic activity of the solutions was determined five times over a period of 13 days. The enzymatic stability of these solutions was compared with the enzymatic stability of a solution without oxalate.

TABLE 2

| time | Enzymatic Activity (mOD/min.) Oxalate concentration: | | | | | |
|---|---|---|---|---|---|---|
| (h) | 0 mM | 1 mM | 2 mM | 4 mM | 8 mM | 16 mM |
| 0 | 14.47 | 13.76 | 13.63 | 12.87 | 11.86 | 10.37 |
| 68.5 | 10.75 | 11.47 | 12.08 | 11.90 | 11.34 | 10.15 |
| 148 | 10.43 | 11.01 | 11.07 | 11.36 | 10.86 | 9.72 |
| 199 | 8.93 | 9.89 | 9.92 | 10.36 | 9.84 | 8.81 |
| 319 | 7.43 | 8.67 | 8.63 | 9.60 | 9.33 | 8.65 |
| t½ (days) | 14.8 | 21.0 | 20.2 | 31.2 | 36.5 | 45.6 |

Table 2 shows the results from the spectrophotometrical measurements (OD: Optical Density) and the calculated $t_{1/2}$ values. The $t_{1/2}$ values for the solutions clearly show that the presence of oxalate has a remarkably positive effect on the stability. For the highest concentration, 16 mM, the stability (quoted as $t_{1/2}$) was tripled. Thus, the slightly lower initial specific enzymatic activity is fully compensated for after 8–9 days.

We claim:

1. An enzyme sensor for measuring the concentration or activity of an analyte in a test fluid, the sensor having at least one enzyme layer comprising an immobilized enzyme for which the analyte is a substrate, the immobilized enzyme being obtained by formation of one or more covalent link(s), optionally by using a cross-linking agent, between the enzyme and at least one type of macromolecule in the presence of a competitive inhibitor for said enzyme.

2. The enzyme sensor according to claim 1, wherein the enzyme layer is included in a membrane of the enzyme sensor.

3. The enzyme sensor claim 1, wherein the enzyme is selected from enzymes for which a substance selected from the group consisting of glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine is a substrate.

4. The enzyme sensor according to claim 1, wherein the enzyme is lactate oxidase.

5. The enzyme sensor according to claim 1, wherein the enzyme is immobilized to a macromolecule selected from the group consisting of albumins and albumin derivatives, such as bovine serum albumin, bovine serum albumin-cysteinyl, conalbumin (ovotransferrin), and ovalbumin (egg white albumin).

6. The enzyme sensor according to claim 1, wherein the initial specific enzymatic activity of the immobilized enzyme is at least 50% of the initial specific enzymatic activity of a corresponding amount of non-immobilized enzyme.

7. The enzyme sensor according to claim 1, wherein the enzyme is lactate oxidase and the competitive inhibitor is selected from the group consisting of oxalacetate, oxalate, α-hydroxy-sulphonate, bisulphite, and phenylacetate.

8. The enzyme sensor according to claim 7, wherein the competitive inhibitor is oxalate.

9. The enzyme sensor according to claim 1, wherein the initial specific enzymatic activity of the immobilized enzyme is at least 1.5 times the initial specific enzymatic activity of a corresponding amount of enzyme immobilized to the same kind of macromolecule by using, if applicable, the same kind of cross-linking agent in the absence of a competitive inhibitor for said enzyme.

10. A membrane for an enzyme sensor for measuring the concentration or activity of an analyte in a test fluid, said membrane having at least one enzyme layer comprising an immobilized enzyme for which the analyte is a substrate, the immobilized enzyme being obtained by formation of one or more covalent link(s), optionally by using a cross-linking agent, between the enzyme and at least one type of macromolecule in the presence of a competitive inhibitor for said enzyme.

11. The membrane according to claim 10, wherein the enzyme is selected from enzymes for which a substance selected from the group consisting of glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine is a substrate, the enzyme preferably being lactate oxidase.

12. The membrane according to claim 10, wherein the enzyme is immobilized to a macromolecule selected from the group consisting of albumins and albumin derivatives, such as bovine serum albumin, bovine serum albumin-cysteinyl, conalbumin (ovotransferrin), and ovalbumin (egg white albumin).

13. The membrane according to claim 10, wherein the enzyme is lactate oxidase and the competitive inhibitor is selected from the group consisting of oxalacetate, oxalate, α-hydroxy-sulphonate, bisulphite, and phenylacetate, the competive inhibitor is oxalate.

14. A method for improving the stability of the enzymatic activity of an immobilized enzyme included in an enzyme sensor for measuring the concentration of an analyte in a test fluid, the analyte being a substrate for said enzyme, the method comprising intermittently or continuously exposing the immobilized enzyme to a solution comprising a competitive inhibitor for said enzyme.

15. The method according to claim 14, wherein the immobilized enzyme is included in a membrane of the enzyme sensor.

16. The method according to claim 14, wherein the enzyme is exposed to a solution comprising a competitive inhibitor for said enzyme between each or substantially each measurement, or between each or substantially each series of measurements, of the analyte.

17. The method according to claim 16, wherein the solution comprising the competitive inhibitor is a rinse fluid for said sensor.

18. The method according to claim 14, wherein the enzyme is selected from enzymes for which a substance selected from the group consisting of glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine is a substrate.

19. The method according to claim 18, wherein the enzyme is lactate oxidase.

20. The method according to claim 19, wherein the competitive inhibitor is selected from the group consisting of oxalacetate, oxalate, α-hydroxy-sulphonate, bisulphite, and phenylacetate.

21. The method according to claim 20, wherein the competitive inhibitor is oxalate.

22. A stabilizing agent for an immobilized enzyme included in an enzyme sensor of a solution comprising a competitive inhibitor for said enzyme wherein the enzyme sensor is adapted for measuring the concentration or activity of an analyte in a test fluid, the analyte being a substrate for the enzyme.

23. The agent according to claim 22, wherein the immobilized enzyme is included in a membrane of the enzyme sensor.

24. The agent according to claim 22, wherein the enzyme is selected from enzymes for which a substance selected from the group consisting of glucose, cholesterol, lactate, creatine, creatinine, urea, uric acid, pyruvate, alcohols, bilirubin, ascorbate, phosphate, proteins, triglycerides, phenylalanine, tyrosine, and hypoxanthine is a substrate.

25. The agent according to claim 24, wherein the enzyme is lactate oxidase and the analyte is lactate.

26. The agent according to claim 25, wherein the competitive inhibitor is selected from the group consisting of oxalacetate, oxalate, α-hydroxy-sulphonate, bisulphite, and phenylacetate.

27. The agent according to claim 26 wherein the competitive inhibitor is oxalate.

28. The agent according to claim 22, wherein the solution comprising the competitive inhibitor is a rinse fluid for said sensor.

29. An apparatus for measuring the concentration or activity of one or more analyte(s) in a test fluid, the apparatus comprising an enzyme sensor having at least one layer of an immobilized enzyme for which at least one of the analytes is a substrate, wherein the apparatus further comprises one or more containers with solution(s) needed for the operation of the apparatus, at least one solution comprising a competitive inhibitor for the enzyme, and means for intermittently exposing the sensor to the solution comprising the competitive inhibitor.

30. The apparatus according to claim 29, wherein the immobilized enzyme is included in a membrane of the enzyme sensor.

31. The apparatus according to claim 29, wherein the solution comprising the competitive inhibitor is a rinse fluid for said sensor.

32. The apparatus according to claim 29, wherein the analyte is lactate, the enzyme is lactate oxidase and the competitive inhibitor of the solution is oxalate.

* * * * *

UNITED STATES PATENT AND TRADEMARK OFFICE
CERTIFICATE OF CORRECTION

PATENT NO. : 6,051,389
DATED : April 18, 2000
INVENTOR(S) : Thomas AHL, et al.

It is certified that error appears in the above-indentified patent and that said Letters Patent is hereby corrected as shown below:

Column 15, line 34 (line 1 of claim 3), after "sensor" insert --according to--.

Signed and Sealed this

Sixth Day of March, 2001

Attest:

NICHOLAS P. GODICI

*Attesting Officer*  Acting Director of the United States Patent and Trademark Office